United States Patent
Walker

(10) Patent No.: US 9,162,221 B1
(45) Date of Patent: Oct. 20, 2015

(54) HETEROGENEOUS LIQUID PHASE CATALYTIC PROCESS FOR THE DEHYDRATION OF MONOETHANOLAMINE TO ETHYLENIMINE

(71) Applicant: John Henry Walker, Lake Jackson, TX (US)

(72) Inventor: John Henry Walker, Lake Jackson, TX (US)

(73) Assignee: John Henry Walker, Lake Jackson, TX (US)

( * ) Notice: Subject to any disclaimer, the term of this patent is extended or adjusted under 35 U.S.C. 154(b) by 0 days.

(21) Appl. No.: 14/015,472

(22) Filed: Aug. 30, 2013

Related U.S. Application Data

(60) Provisional application No. 61/702,977, filed on Sep. 19, 2012.

(51) Int. Cl.
*C07D 203/04* (2006.01)
*B01J 31/08* (2006.01)
*B01J 19/00* (2006.01)
*C07D 203/02* (2006.01)

(52) U.S. Cl.
CPC .... *B01J 31/08* (2013.01); *B01J 19/00* (2013.01); *C07D 203/02* (2013.01)

(58) Field of Classification Search
USPC .......................................... 548/954; 544/358
See application file for complete search history.

(56) References Cited

U.S. PATENT DOCUMENTS

| | | | | |
|---|---|---|---|---|
| 2,773,742 A | * | 12/1956 | Connor, Jr. | 423/387 |
| 4,289,656 A | * | 9/1981 | Hayes et al. | 502/311 |
| 4,301,036 A | * | 11/1981 | Childress et al. | 502/254 |
| 4,337,175 A | * | 6/1982 | Ramirez | 502/340 |
| 4,376,732 A | | 3/1983 | Ramirez | |
| 4,477,591 A | | 10/1984 | Ramirez | |
| 6,017,969 A | * | 1/2000 | Jones et al. | 521/32 |
| 2004/0121902 A1 | * | 6/2004 | Chang et al. | 502/208 |
| 2009/0149417 A1 | * | 6/2009 | Ossovskaya et al. | 514/49 |

FOREIGN PATENT DOCUMENTS

| | | | |
|---|---|---|---|
| JP | 08-089819 | * | 4/1996 |
| JP | 08-187436 | * | 7/1996 |
| JP | 10-211433 | * | 8/1998 |

OTHER PUBLICATIONS

Hideaki Tsuneki; Acid-Base Catalysis: On the Example of Ethylenimine Production; Applied Catalysis A: General 221, Nov. 2001, pp. 209-217, total 9 pages.

Henry Wenker, J. Am. Chem. Soc., Nov. 1935, 57 (11), p. 2328, total 1 page.

Masahiro Kato, et al.; Effects of the Intramolecular NH-S Hydrogen Bond in Mononuclear Plantinum (II) and Palladium (II) Complexes With 2,2'-Bipyridine and Benzenethiol Derivatives; Inorganic Chemistry, vol. 44, No. 6, 2005, Feb. 22, 2005, pp. 1966-1972, total 7 pages.

* cited by examiner

*Primary Examiner* — Peter D Mulcahy
*Assistant Examiner* — Henry Wu
(74) *Attorney, Agent, or Firm* — Greenberg Traurig, LLP; Ross Spencer Garsson

(57) ABSTRACT

A novel heterogeneous liquid phase catalytic process for dehydration of monoethanolamine to ethylenimine and water has been discovered. The process utilizes a novel catalyst made by modifying a cation exchange resin in the hydrogen ion form. The process using the catalyst is performed in a solution of monoethanolamine in a solvent.

17 Claims, 1 Drawing Sheet

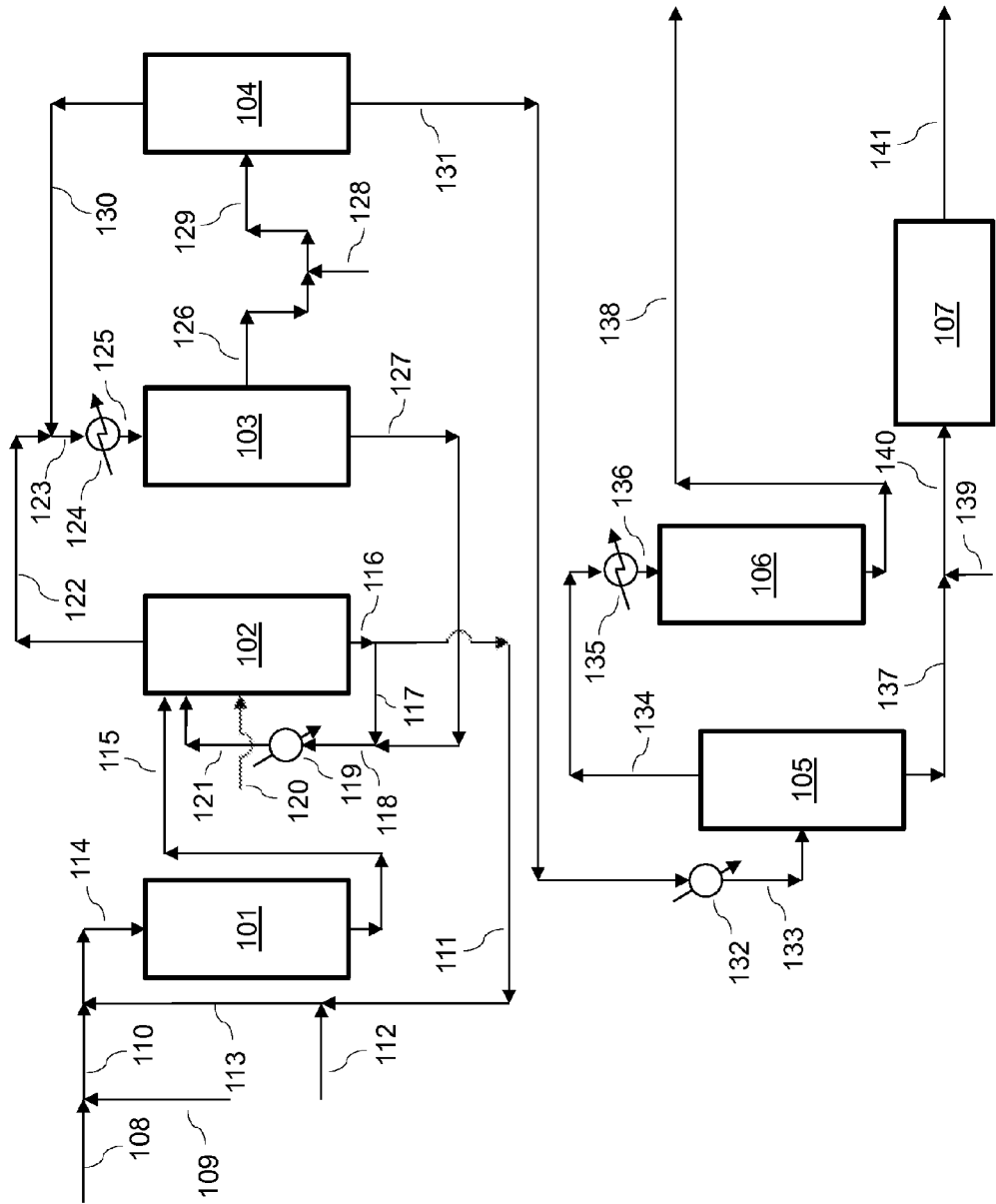

HETEROGENEOUS LIQUID PHASE CATALYTIC PROCESS FOR THE DEHYDRATION OF MONOETHANOLAMINE TO ETHYLENIMINE

CROSS-REFERENCE TO RELATED PATENT APPLICATIONS

This application claims priority to provisional U.S. Patent Application Ser. No. 61/702,977, filed Sep. 19, 2012, entitled "Heterogeneous Liquid Phase Catalytic Process For The dehydration of Monoethanolamine to Ethylenimine," which provisional patent application is commonly owned by the Applicant of the present invention and is hereby incorporated herein by reference in its entirety for all purposes.

TECHNICAL FIELD

The present invention relates to a heterogeneous liquid phase catalytic process for dehydration of monoethanolamine to ethylenimine and water. The present invention utilizes a novel catalyst made by modifying a cation exchange resin in the hydrogen ion form. The heterogeneous liquid phase catalytic process is performed in a solution of monoethanolamine in a solvent.

BACKGROUND

Ethylenimine (EI) is an active three-membered cyclic amine and is a very useful compound since it can introduce an amino group by an addition reaction, substitution reaction, ring opening reaction and the like. EI is a commercial chemical used as raw material in pharmaceutical and amino resins. EI can also be used to determine the desired product mix of alkylene amines (ethylenediamine, diethylenetriamine and triethylenetetramine, etc.) when reacting with ammonia. The current alkylene amines process based on ethylene dichloride and ammonia gives no product flexibility.

EI has been formed by catalytic dehydration of monoethanolamine (MEA) in a vapor phase over a catalyst. Examples of such processes are disclosed and taught in U.S. Pat. Nos. 4,289,656, 4,301,036, and 4,337,175.

Hideaki Tsuneki, "Acid-base catalysis: on the example of ethylenimine production," *Applied Catalysis A: General*, 2001, 221, 209-217 discusses certain solid acid-base catalysts showing high catalytic activity and selectivity in vapor phase intramolecular dehydration of MEA to EI.

Operating a vapor phase has problems because catalytic performance (selectivity and life of the catalyst) can be issues and also processes need to be performed at high process temperatures.

EI has also been produced from MEA in the liquid phase by using $H_2SO_4$ and NaOH (Wenker reaction). However, this reaction forming large quantify of waste water containing by-product $Na_2SO_4$ in the process, which can be a problem.

Accordingly, there is a need for an improved low temperature liquid phase catalytic process for the dehydration of MEA to EI and water.

SUMMARY OF THE INVENTION

Applicant has discovered a novel catalyst for the heterogeneous liquid phase dehydration of MEA to EI and water. In embodiments of the present invention, the catalyst is made by modifying a cation exchange resin in the hydrogen ion form using two cations which modify the resin in different positions (i.e., different parts of the resin). These two other cations are exchanged onto the resin. The first cation can be aqua-diethylenetriamine platinum II ($[Pt(dien)(H_2O)]^2$). The second cation can be ionic (neutralized) mercaptoethylamine, ($SH-CH_2-CH_2-NH_3^+$).

The ratio of the two cations utilized in to form the catalyst can be controlled and optimized based upon the parameters. In some embodiments, the amount of each of the cations utilized is such that each cation occupies approximately 20% of the hydrogen ion sites of the resin (thus, in this embodiment, leaving approximately 60% of the resin as hydrogen ions).

The reaction (MEA to EI and water) can be accomplished in a solution (generally a dilute solution) of monoethanolamine in a solvent (generally an inert solvent, such as methylene chloride, $MeCl_2$).

Once the liquid phase catalytic process takes place, the products and the reactants can be separated to isolate the produced EI.

In general, in one aspect, the invention features a process that includes selecting a hydrogen ion exchange resin. The process further includes modifying the hydrogen ion exchange resin using a first cation and a second cation to form a resin catalyst. The first cation and the second cation modify the hydrogen ion exchange resin at different parts of the hydrogen ion exchange resin. The first cation is a cation that is a complex with $d^8$ electron configuration. The second cation is a mercaptan. The process further includes charging a solution of monoethanolamine and solvent into a reactor. The resin catalyst is in the reactor. The process further includes performing a heterogeneous liquid phase catalytic process in the reactor using the resin catalyst to dehydrate the monoethanolamine to form ethylenimine. The process further includes discharging the ethylenimine from the reactor. The process further includes collecting the ethylenimine.

Implementations of the invention can include one or more of the following features:

The first cation can include aqua-diethylenetriamine platinum II.

The second cation can include mercaptoethylamine.

The hydrogen ion exchange resin can include a plurality of hydrogen ion sites. The step of modifying the hydrogen ion exchange resin can include the first cation occupying between 10% and 30% of the plurality of hydrogen ion sites of the hydrogen ion exchange resin. The step of modifying the hydrogen ion exchange resin can include the second cation occupying between 10% and 30% of the plurality of hydrogen ion sites of the hydrogen ion exchange resin.

The step of modifying the hydrogen ion exchange resin can include the first cation occupying between 15% and 25% of the plurality of hydrogen ion sites of the hydrogen ion exchange resin. The step of modifying the hydrogen ion exchange resin can include the second cation occupying between 15% and 25% of the plurality of hydrogen ion sites of the hydrogen ion exchange resin.

The hydrogen ion exchange resin can include a plurality of hydrogen ion sites. The step of modifying the hydrogen ion exchange resin can include the first cation and the second cation collectively occupying between 20% and 60% of the plurality of hydrogen ion sites of the hydrogen ion exchange resin.

The step of modifying the hydrogen ion exchange resin can include the first cation and the second cation collectively occupying between 30% and 50% of the plurality of hydrogen ion sites of the hydrogen ion exchange resin.

The step of modifying the hydrogen ion exchange resin can include sequentially adding the first cation and the second cation to the hydrogen ion exchange resin.

The step of modifying the hydrogen ion exchange resin can include adding the first cation to the hydrogen ion exchange resin before adding the second cation to the hydrogen exchange resin.

The step of modifying the hydrogen ion exchange resin can include cumulatively adding the first cation and the second cation to the hydrogen ion exchange resin.

The solvent can include $MeCl_2$.

The step of discharging the ethylenimine from the reactor can include flowing a stream comprising ethylenimine and other materials, wherein the other materials are non-reacted monoethanolamine, solvent, water, or a combination thereof.

The step of collecting the ethylenimine can include separating the ethylenimine from the other materials.

The other materials can include a combination of non-reacted monoethanolamine, solvent, and water. The process can further include separating ethylenimine, non-reacted monoethanolamine, solvent, and water from each other.

The process can further include recycling at least one of the non-reacted monoethanolamine and the solvent in the process.

The reactor can be at a temperature between 40° C. and 60° C.

The reactor can be at a temperature between −20° C. and 40° C.

The hydrogen ion exchange resin can be a gel type resin or a macroporous resin.

The step of modifying the hydrogen ion exchange resin can include mixing the hydrogen ion exchange resin and water to form a mixture. The step of modifying the hydrogen ion exchange resin can further include adding the first cation and the second cation to the mixture to form a second mixture. The step of modifying the hydrogen ion exchange resin can further include draining some of the water from the second mixture to form a wet resin. The step of modifying the hydrogen ion exchange resin can further include adding the solvent to the wet resin. The step of modifying the hydrogen ion exchange resin can further include heating the mixture at the boiling point to remove the remaining water from the wet resin to form the resin catalyst. The resin catalyst can then be charged to the reactor.

The first cation can include aqua-diethylenetriamine platinum II. The second cation can include mercaptoethylamine. The solvent can include $MeCl_2$. The step of modifying the hydrogen ion exchange resin can further include the first cation and the second cation collectively occupying between 20% and 60% of the plurality of hydrogen ion sites of the hydrogen ion exchange resin.

In general, in another aspect, the invention features a process that includes selecting a hydrogen ion exchange resin. The process further includes modifying the hydrogen ion exchange resin using a first cation and a second cation to form a resin catalyst. The first cation and the second cation modify the hydrogen ion exchange resin at different parts of the hydrogen ion exchange resin. The first cation is a cation that is a complex with $d^8$ electron configuration. The second cation is a phosphine. The process further includes charging a solution of monoethanolamine and solvent into a reactor. The resin catalyst is in the reactor. The process further includes performing a heterogeneous liquid phase catalytic process in the reactor using the resin catalyst to dehydrate the monoethanolamine to form ethylenimine. The process further includes discharging the ethylenimine from the reactor. The process further includes collecting the ethylenimine.

Implementations of the invention can include one or more of the following features:

The first cation can include aqua-diethylenetriamine platinum II.

In general, in another aspect, the invention features a catalyst that includes a hydrogen ion exchange resin comprising a plurality of hydrogen ion sites. The catalyst further includes a first cation including a cation that is a complex with $d^8$ electron configuration. The first cation occupies at least some of the plurality of the hydrogen ion sites of the hydrogen ion exchange resin at a first portion of the hydrogen ion exchange resin. The catalyst further includes a second cation including a cation that is a mercaptan or a phosphine. The second cation occupies at least some of the plurality of the hydrogen ion sites of the hydrogen ion exchange resin at a second portion of the hydrogen ion exchange resin. The catalyst is operable for catalyzing a heterogeneous liquid phase process to dehydrate monoethanolamine to ethylenimine.

Implementations of the invention can include one or more of the following features:

The first cation can include aqua-diethylenetriamine platinum II. The second cation can include mercaptoethylamine.

The first cation can be occupying between 15% and 25% of the plurality of hydrogen ion sites of the hydrogen ion exchange resin. The second cation can be occupying between 15% and 25% of the plurality of hydrogen ion sites of the hydrogen ion exchange resin.

In general, in another aspect, the invention features a system that includes a reactor operable for dehydrating monoethanolamine in a solution of solvent to form ethylenimine. The reactor is charged with a catalyst. The catalyst includes a hydrogen ion exchange resin comprising a plurality of hydrogen ion sites. The catalyst further includes a first cation including a cation that is a complex with $d^8$ electron configuration. The first cation occupies at least some of the plurality of the hydrogen ion sites of the hydrogen ion exchange resin at a first portion of the hydrogen ion exchange resin. The catalyst further includes a second cation including a cation that is a mercaptan or a phosphine. The second cation occupies at least some of the plurality of the hydrogen ion sites of the hydrogen ion exchange resin at a second portion of the hydrogen ion exchange resin. The catalyst is operable for catalyzing a heterogeneous liquid phase process to dehydrate monoethanolamine to ethylenimine. The system further includes a first conduit connected to the reactor that is operable to allow an input stream of the solution of solvent and monoethanolamine to flow into the reactor. The system further includes a second conduit connected to the reactor that is operable to allow an output stream comprising ethylenimine formed in the reactor to flow out of the reactor.

Implementations of the invention can include one or more of the following features:

The system can further include a separation system. The separation system can be operable to separate the ethylenimine from other materials in the output stream. The other materials can be non-reacted monoethanolamine, solvent, water, and a combination thereof.

The first cation can include aqua-diethylenetriamine platinum II. The second cation can include mercaptoethylamine.

The first cation can be occupying between 15% and 25% of the plurality of hydrogen ion sites of the hydrogen ion exchange resin. The second cation can be occupying between 15% and 25% of the plurality of hydrogen ion sites of the hydrogen ion exchange resin.

There has thus been outlined, rather broadly, the more important features of the invention in order that the detailed description thereof may be better understood, and in order that the present contribution to the art may be better appreciated. There are additional features of the invention that will be described hereinafter.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

DESCRIPTION OF DRAWINGS

FIG. 1 depicts an embodiment of the present invention of a heterogeneous liquid phase catalytic process for the dehydration of MEA to EI and water and the separation and recovery of the products and non-reacted reactants.

DETAILED DESCRIPTION

The present invention is a novel catalyst and process for the heterogeneous liquid phase dehydration of MEA to EI and water. The catalyst is made by modifying a cation exchange resin in the hydrogen ion form using two cations which modify the resin in different positions (i.e., different parts of the resin). Generally, these modifications occur at different sites of the resin (which is controlled by cation and the place on the resin upon which the exchange occurs due to that cation).

With regard to the hydrogen ion exchange resin, either a gel type resin or a macroporous resin may be used.

The first cation is aqua-diethylenetriamine platinum II ([Pt(dien)(H$_2$O)]$^2$). The second cation can be ionic (neutralized) mercaptoethylamine (SH—CH$_2$—CH$_2$—NH$_3^+$).

The first and second cations can be added sequentially or cumulatively to the resin. In some embodiments, the aqua-diethylenetriamine platinum II is first added to the resin such that it occupies a certain percentage of the hydrogen ion sites. Thereafter, the ionic (neutralized) mercaptoethylamine (as, e.g., mercaptoethylamine hydrochloride) is then added to the mixture. The solutions of these cations can be added to a mixture of de-ionized water and resin at room temperature. This is typically done outside the reaction vessel. The water is drained from the resin. Solvent (e.g., MeCl$_2$) is added to the wet resin. The mixture is then heated at the boiling point until all of the water is removed overhead by the azeotrope. The resin (catalyst) is then charged to the reactor.

With respect to the amount of first cations used, in some embodiments, the certain percentage occupied using the first cation is typically between about 10% to about 30% of the resin's hydrogen ion sites. In further embodiments, the certain percentage occupied using the first cation is more typically between about 15% to about 25% of the resin's hydrogen ion sites. Most typically, the certain percentage occupied by the first cation is approximately 20%.

With respect to the amount of second cation used, in some embodiments, the certain percentage occupied using the second cation is typically between about 10% to about 30% of the resin's hydrogen ion sites. In further embodiments, the certain percentage occupied using the second cation is more typically between about 15% to about 25% of the resin's hydrogen ion sites. Most typically, the certain percentage occupied by the second cation is approximately 20%.

Generally, the aggregate amount of hydrogen ion sites of the resin occupied by the first and second cations is between 20% to 60%, more typically 30% to 50%, and most typically approximately 40%.

The amount of first and second cations can be dependent on reactor conditions and process design. Aqua-diethylenetriamine platinum II is a complex with d$^8$ electron configuration. It is four coordinate with square planar geometry. Water is the leaving group. In this complex, the three other coordination positions are kept constant using the inert dien ligand. The amine end of MEA (being nucleophilic) attacks the complex from either side of the plane. This forms initially a square pyramidal species. It can form five and six coordinated species. The mercaptan forms a weak bond with a hydrogen atom on the complexed amine. Researchers at Osaka University in Japan found a NH—S bond in mononuclear platinum(II) and palladium(II) with 2,2"-bipyridine and benzenethiol derivatives [M. Kato, et al., "Effects of the Intramolecular NH—S Hydrogen Bond in Mononuclear Platinum(II) and Palladium (II) Complexes with 2,2'-Bipyridine and Benzenethiol Derivatives," *Inorg. Chem.*, 2005, 44(6), 1966-72]. This will create a partial negative charge on the complex. The OH group (being uncomplexed) is protonated by a nearby hydrogen ion from the resin. As the water molecule leaves, the carbocation formed is attracted to the partial negative on the complex. The ring closes (thus forming EI).

Such reaction is shown below:

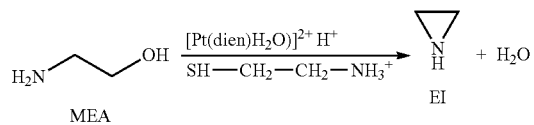

The second cation can be a mercaptan (i.e., an organosulfur compound that contains a carbon-bonded sulfhydryl (—C—SH or R—SH) group that forms a weak bond on with the hydrogen atom on the complexed amine of MEA. Alternatively, a possible second cation could be a phoshine like Ph$_2$-CH$_2$—CH$_2$-Ph$_3^+$, since a phosphine, in some cases, has been known to have strong coordinating power.

FIG. 1 depicts an embodiment of the present invention of a heterogeneous liquid phase catalytic process for the dehydration of MEA to EI and water and the separation and recovery of the products and non-reacted reactants.

In this embodiment shown in FIG. 1, stream 108 containing MEA is combined with stream 109 containing a solvent (such as inert solvent MeCl$_2$) to form steam 110 of a solution (generally a dilute solution) of MEA for use in the reaction vessel 101. As shown in FIG. 1, recycled stream 111 (having MEA and the solvent, such as MeCl$_2$) can be combined with stream 112 (which contains additional MEA) to form stream 113, which stream 113 and stream 110 are combined to form stream 114. Generally, stream 114 will have between 0.1% to 10% by weight of MEA. These recycle stream 111 and the additional MEA stream 112 are optional. Moreover, while not shown in the FIG. 1, the temperature of the stream 114 can be raised to a low temperature, such as around 60° C. (such as a steaming device). The resulting dilute solution in stream 114 is then introduced into reactor 101 and the liquid catalytic process occurs to dehydrate MEA to form EI and water. The products of this reaction and the non-reacted reactants flow from the reactor 101 in stream 115.

Stream 115 flows to a stripper/distillation column 102 with output streams stream 122 and stream 116. Stream 122 includes EI, water, MeCl$_2$, as an azeotrope. Stream 116 includes MeCl$_2$ and non-reacted MEA.

Stream 116 can be split into stream 111 (which is recycled back for combination with stream 112 as discussed above) and stream 117. Stream 117 can be combined with recycle stream 127 (discussed below) to form stream 118. Stream 118 can be heated (such as by heating device 119) to form stream 121, which is reintroduced back into stripper/distillation column 102. Optionally a stream 120 of steam can also be introduced into stripper/distillation column 102. This is to insure that all of the EI is azeotroped overhead.

As for stream 122, this stream 122 can be combined with stream 130 (discussed below) to form stream 123. Stream 123 flows through a condenser 124 to form stream 125, which flows to a separator 103. In separator 103 phases are formed of (a) EI and water and (b) EI and then solvent (MeCl$_2$). The output streams from separator 103 are stream 126 (containing EI, water, and residual MeCl$_2$) and stream 127 (containing EI, MeCl$_2$, and residual water). As discussed above, stream 127 is recycled for combination with stream 117 to form steam 118.

As for stream 126, a stream 128 of NaOH (such as at 50%) can added to form stream 129 stream to give a 4% solution of NaOH in stream 129. The purpose of NaOH is to stabilize the product EI. Stream 129 then flows to stripper 104. The output streams from stripper 104 are stream 130 (containing the azeotrope that is recycled by combining it with stream 122 to form stream 123) and stream 131.

Stream 131 includes EI, water, and generally around 4% NaOH. Stream 131 can be heated (such as by heating device 132) to form stream 133, which flows to a distillation column 105. Distillation column 105 has outputs streams stream 134 and stream 137.

Output stream 134 (which contains EI) flows to a condenser 135 to form stream 136, which flows to product tank 106. Product tank 106 has an output stream 138 containing the EI, which can then be sent to storage (storage of the EI).

Output stream 137 can then be combined stream 139 (having concentrated HCl) to form steam 140. Stream 140 can then be utilized in a process 107 to properly get rid of the carbon in that stream. As shown in FIG. 1, process 107 is a Zimpros wet air oxidation process (Siemens). Output stream 141 contains CO$_2$ and N$_2$.

A number of embodiments of the invention have been described. Nevertheless, it will be understood that various modifications may be made without departing from the spirit and scope of the invention. Accordingly, other embodiments are within the scope of the following claims.

While embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, other embodiments are within the scope of the following claims. The scope of protection is not limited by the description set out above, but is only limited by the claims which follow, that scope including all equivalents of the subject matter of the claims.

The disclosures of all patents, patent applications, and publications cited herein are hereby incorporated herein by reference in their entirety, to the extent that they provide exemplary, procedural, or other details supplementary to those set forth herein.

What is claimed is:

1. A catalyst comprising:
   (a) a hydrogen ion exchange resin comprising a plurality of hydrogen ion sites, wherein
      (i) a first portion of the plurality of the hydrogen ion sites are located on a first portion of the hydrogen ion exchange resin, and
      (ii) a second portion of the plurality of the hydrogen ion sites are located on a second portion of the hydrogen ion exchange resin;
   (b) a first cation comprising a cation that is a complex with d$^8$ electron configuration, wherein the first cation occupies at least some of the hydrogen ion sites of the first portion of the plurality of the hydrogen ion sites located on the first portion of the hydrogen ion exchange resin; and
   (c) a second cation comprising a cation selected from the group consisting of an ionic or neutralized mercaptan and an ionic or neutralized phosphine, wherein
      (i) the second cation comprises NH$_3^+$ or PH$_3^+$, and
      (ii) the second cation occupies at least some the hydrogen ion sites of the second portion of the plurality of the hydrogen ion sites located on the second portion of the hydrogen ion exchange resin,
   wherein the catalyst is operable for catalyzing a heterogeneous liquid phase process to dehydrate monoethanolamine to ethylenimine.

2. The catalyst of claim 1, wherein
   (a) the first cation comprises aqua-diethylenetriamine platinum II; and
   (b) the second cation comprises ionic mercaptoethylamine (HS—CH$_2$—CH$_2$—NH$_3^+$.

3. The catalyst of claim 2, wherein
   (a) the first cation occupies between 15% and 25% of the plurality of hydrogen ion sites of the hydrogen ion exchange resin; and
   (b) the second cation occupies between 15% and 25% of the plurality of hydrogen ion sites of the hydrogen ion exchange resin.

4. The catalyst of claim 1, wherein the first cation comprises aqua-diethylenetriamine platinum II.

5. The catalyst of claim 1, wherein the second cation comprises the ionic or neutralized mercaptan.

6. The catalyst of claim 1, wherein the second cation comprises ionic mercaptoethylamine (HS—CH$_2$—CH$_2$—NH$_3^+$.

7. The catalyst of claim 1, wherein the second cation comprises the ionic or neutralized phosphine.

8. The catalyst of claim 1, wherein
   (a) the first cation occupies between 10% and 30% of the plurality of hydrogen ion sites of the hydrogen ion exchange resin; and
   (b) the second cation occupies between 10% and 30% of the plurality of hydrogen ion sites of the hydrogen ion exchange resin.

9. The catalyst of claim 1, wherein
   (a) the first cation occupies between 15% and 25% of the plurality of hydrogen ion sites of the hydrogen ion exchange resin; and
   (b) the second cation occupies between 15% and 25% of the plurality of hydrogen ion sites of the hydrogen ion exchange resin.

10. The catalyst of claim 1, wherein the hydrogen ion exchange resin comprises the first cation and the second cation collectively occupying between 20% and 60% of the plurality of hydrogen ion sites of the hydrogen ion exchange resin.

11. The catalyst of claim 1, wherein the hydrogen ion exchange resin comprises the first cation and the second cation collectively occupying between 30% and 50% of the plurality of hydrogen ion sites of the hydrogen ion exchange resin.

12. The catalyst of claim 1, wherein the hydrogen ion exchange resin is a gel type resin or a macroporous resin.

13. The catalyst of claim 1, wherein the catalyst is operable for catalyzing the heterogeneous liquid phase process to dehydrate the monoethanolamine to ethylenimine while in a solution of the monoethanolamine and a solvent.

14. The catalyst of claim 1, wherein the catalyst is operable for catalyzing the heterogeneous liquid phase process to dehydrate the monoethanolamine to ethylenimine while in a solution of the monoethanolamine and methylene chloride $CH_2Cl_2$.

15. The catalyst of claim 1, wherein the catalyst is operable for catalyzing the heterogeneous liquid phase process to dehydrate the monoethanolamine to ethylenimine at a temperature between 40° C. and 60° C.

16. The catalyst of claim 1, wherein the catalyst is operable for catalyzing the heterogeneous liquid phase process to dehydrate the monoethanolamine to ethylenimine at a temperature between −20° C. and 40° C.

17. The catalyst of claim 1, wherein the second cation comprises $PH_2-CH_2-CH_2-PH_3^+$.

\* \* \* \* \*